US011826144B2

(12) United States Patent
Lee et al.

(10) Patent No.: US 11,826,144 B2
(45) Date of Patent: *Nov. 28, 2023

(54) APPARATUS AND METHOD FOR ESTIMATING BIOLOGICAL SUBSTANCE, APPARATUS FOR ACQUIRING UNIT SPECTRUM, AND WEARABLE DEVICE

(71) Applicant: SAMSUNG ELECTRONICS CO., LTD., Suwon-si (KR)

(72) Inventors: So Young Lee, Daejeon (KR); Jin Young Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 383 days.

This patent is subject to a terminal disclaimer.

(21) Appl. No.: 17/137,575

(22) Filed: Dec. 30, 2020

(65) Prior Publication Data

US 2021/0161432 A1 Jun. 3, 2021

Related U.S. Application Data

(62) Division of application No. 15/359,752, filed on Nov. 23, 2016, now Pat. No. 10,918,319.

(30) Foreign Application Priority Data

Jul. 25, 2016 (KR) .......................... 10-2016-0094288

(51) Int. Cl.
*A61B 5/1455* (2006.01)
*G01N 21/35* (2014.01)
(Continued)

(52) U.S. Cl.
CPC .......... *A61B 5/1455* (2013.01); *A61B 5/0002* (2013.01); *A61B 5/0075* (2013.01);
(Continued)

(58) Field of Classification Search
CPC ..... A61B 5/0075; A61B 5/1455; A61B 5/681; A61B 2562/0238; G01N 21/65
See application file for complete search history.

(56) References Cited

U.S. PATENT DOCUMENTS

| 5,553,616 A | 9/1996 | Ham |
| 5,957,841 A | 9/1999 | Maruo et al. |

(Continued)

FOREIGN PATENT DOCUMENTS

| CN | 201519152 U | 7/2010 |
| JP | 3902999 B2 | 4/2007 |

(Continued)

OTHER PUBLICATIONS

K. Yamakoshi, et al.: "Pulse glucometry: a new approach for noninvasive blood glucose measurement using instantaneous differential near-infrared spectrophotometry", Journal of Biomedical Optics, vol. 11, No. 5 (Sep. 1, 2006), total 10 pages.

(Continued)

*Primary Examiner* — Puya Agahi
(74) *Attorney, Agent, or Firm* — Sughrue Mion, PLLC

(57) ABSTRACT

An apparatus for estimating a biological substance in a user using a unit spectrum for the biological substance acquired using a biological tissue simulation solution is provided. The apparatus may include a spectrometer configured to emit a light to a skin of a user, detect the light returned from the skin, and measure a skin spectrum of the user from the detected light and a processor configured to estimate a biological substance in the user based on the measured skin spectrum and a unit spectrum acquired using a biological tissue simulation solution.

11 Claims, 17 Drawing Sheets

(51) Int. Cl.
  *G01N 21/65* (2006.01)
  *A61B 5/00* (2006.01)
  *A61B 5/1495* (2006.01)
  *A61B 5/145* (2006.01)
  *G01N 21/3577* (2014.01)

(52) U.S. Cl.
  CPC ........ *A61B 5/1495* (2013.01); *A61B 5/14532* (2013.01); *A61B 5/14546* (2013.01); *A61B 5/443* (2013.01); *A61B 5/4872* (2013.01); *A61B 5/681* (2013.01); *A61B 5/7267* (2013.01); *A61B 5/7275* (2013.01); *A61B 5/7278* (2013.01); *A61B 5/742* (2013.01); *G01N 21/35* (2013.01); *G01N 21/3577* (2013.01); *G01N 21/65* (2013.01); *A61B 2560/0233* (2013.01); *A61B 2560/045* (2013.01); *A61B 2562/0238* (2013.01); *A61B 2562/0242* (2013.01); *A61B 2576/00* (2013.01); *G01N 2201/12* (2013.01)

(56) References Cited

U.S. PATENT DOCUMENTS

| | | |
|---|---|---|
| 7,133,710 B2 | 12/2006 | Acosta et al. |
| 7,310,544 B2 | 12/2007 | Brister et al. |
| 7,460,895 B2 | 12/2008 | Arnold et al. |
| 8,140,139 B2 | 3/2012 | Grata et al. |
| 8,275,433 B2 | 9/2012 | Yamakoshi |
| 8,280,470 B2 | 10/2012 | Milner |
| 9,037,206 B2 | 5/2015 | Grata et al. |
| 10,039,478 B2 | 8/2018 | Kasahara et al. |
| 2002/0123677 A1 | 9/2002 | Miki et al. |
| 2003/0023151 A1 | 1/2003 | Khalil |
| 2006/0063983 A1* | 3/2006 | Yamakoshi .......... G01N 21/359 600/316 |
| 2006/0281982 A1 | 12/2006 | Grata et al. |
| 2008/0228050 A1* | 9/2008 | Hwang .............. A61B 5/14535 600/316 |
| 2009/0247843 A1 | 10/2009 | Xu |
| 2015/0282751 A1 | 10/2015 | Konno |
| 2015/0342508 A1* | 12/2015 | Chong .............. A61B 5/14532 600/323 |
| 2016/0091496 A1* | 3/2016 | Xu .......................... G01J 3/00 385/115 |
| 2017/0027526 A1 | 2/2017 | Maruo |
| 2017/0131212 A1 | 5/2017 | Hamaguchi et al. |

FOREIGN PATENT DOCUMENTS

| | | |
|---|---|---|
| JP | 2007-178414 A | 7/2007 |
| JP | 2015-62716 A | 4/2015 |
| JP | 2015-142663 A | 8/2015 |
| KR | 10-0268968 B1 | 12/2000 |
| KR | 2002-0055364 A | 7/2002 |
| KR | 10-2008-0026159 A | 3/2008 |
| WO | 97/36540 A1 | 10/1997 |
| WO | 2016/035626 A1 | 3/2016 |

OTHER PUBLICATIONS

Communication dated Aug. 3, 2017 by the European Patent Office in counterpart European Application No. 17150918.5.

Olesberg et al., "In Vivo Near-Infrared Spectroscopy of Rat Skin Tissue with Varying Blood Glucose Levels", Analytical Chemistry, Jan. 1, 2006, 9 pages total, vol. 78, No. 1, American Chemical Society.

Communication dated May 18, 2023 by the Korean Intellectual Property Office in Korean Patent Application No. 10-2016-0094288.

* cited by examiner

APPARATUS AND METHOD FOR ESTIMATING BIOLOGICAL SUBSTANCE, APPARATUS FOR ACQUIRING UNIT SPECTRUM, AND WEARABLE DEVICE

CROSS-REFERENCE TO RELATED APPLICATIONS

This application is a divisional application of U.S. patent application Ser. No. 15/359,752, filed on Nov. 23, 2016, which claims priority from Korean Patent Application No. 10-2016-0094288, filed on Jul. 25, 2016 in the Korean Intellectual Property Office, the disclosures of which are incorporated herein by reference in their entireties.

BACKGROUND

1. Field

Apparatuses and methods consistent with exemplary embodiments relate to estimating a biological substance in a non-invasive way, and more particularly, to acquiring a unit spectrum for estimating a biological substance and estimating the biological substance using the acquired unit spectrum.

2. Description of Related Art

Diabetes mellitus is a chronic disease that causes various complications and cannot be easily treated. Thus, the complications should be prevented by regularly checking blood sugar levels. In addition, those who take insulin shots need to check their blood sugar levels because they are at risk for low blood sugar levels and therefore adjustment of insulin dose may be necessary. Generally, an invasive method is used to measure the blood sugar level due to the high reliability of the method. However, there may be pain, inconvenience, and a risk of infection with a disease when blood is collected using a syringe. In recent years, research has been conducted on a method of measuring a blood sugar level in a non-invasive manner using a spectrometer instead of directly collecting blood.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided an apparatus for estimating a biological substance including: a spectrometer configured to emit a light to a skin of a user, detect the light returned from the skin, and measure a skin spectrum of the user from the detected light, and a processor configured to estimate a biological substance in the user based on the measured skin spectrum and a unit spectrum acquired using biological tissue simulation solution.

The spectrometer may measure the skin spectrum based on at least one of infrared spectroscopy and Raman spectroscopy.

The biological tissue simulation solution may include a scatterer that stimulate a light scattering phenomenon in biological tissue and at least one of gelatin, silica, intralipid, and a serum solution.

The processor may be further configured to acquire the unit spectrum by subtracting a pure spectrum from a bio substance spectrum. The pure spectrum may be measured from the biological tissue simulation solution to which the biological substance is not added, and the bio substance spectrum may be measured from the biological tissue simulation solution to which the biological substance is added.

The processor may include a prediction model creation unit configured to collect a background spectrum of the user as learning data and create a prediction model of the biological substance using the collected learning data and a substance estimator configured to estimate the biological substance using the prediction model.

The substance estimator may estimate the biological substance based on a reference value of the biological substance, the unit spectrum, and an output result of the prediction model.

The spectrometer may measure the background spectrum from the skin of a user in a fasting state in a preset calibration cycle or upon the user's request.

The biological substance may include at least one of a blood substance and a skin substance, the blood substance may include at least one of blood sugar, cholesterol, neutral fat, proteins, and uric acid. The skin substance may include at least one of body fat and proteins, and the proteins may include at least one of collagen, keratin, and elastin.

The apparatus may further include an output unit configured to output a result of estimating the biological substance.

The apparatus may further include a main body including the spectrometer and the processor. The main body is wearable by the user.

The main body may further include a display configured to display a result of estimating the biological material to the user.

The main body may further include a communication interface configured to connect the apparatus to an external device via wired or wireless communication and receive the unit spectrum from the external device.

According to an aspect of another exemplary embodiment, there is provided a method of estimating a biological substance including: emitting a light to a skin of a user; detecting the light returned from the skin, and measuring a skin spectrum of the user from the detected light; and estimating a biological substance in the user based on the measured skin spectrum and a unit spectrum acquired using a biological tissue simulation solution.

The measuring the skin spectrum may include measuring the skin spectrum based on at least one of infrared spectroscopy and Raman spectroscopy.

The biological tissue simulation solution may include a scatterer that stimulates a light scattering phenomenon in biological tissue and may include at least one of gelatin, silica, intralipid, and a serum solution.

The unit spectrum may be acquired in a light reflective way, using spectra measured from a biological tissue simulation solution that does not include the biological substance and a biological tissue simulation solution that includes the biological substance. The unit spectrum may be acquired by subtracting a pure spectrum from a bio substance spectrum. The pure spectrum may be measured from the biological tissue simulation solution to which the biological substance is not added, and the bio substance spectrum is measured from the biological tissue simulation solution to which the biological substance is added The estimating the biological substance may include collecting a background spectrum of the user as learning data and creating a prediction model of the biological substance using the collected learning data and may include estimating the biological substance using the prediction model.

The method may further include measuring the background spectrum from the user's skin in a preset calibration cycle or upon the user's request when the user is in a fasting state.

According to an aspect of another exemplary embodiment, there is provided an apparatus for acquiring a unit spectrum including: a receptor configured to receive a biological tissue simulation solution; a reflector configured to reflect a light incident onto the receptor; a spectrometer configured to emit the light into the receptor, detect the light reflected by the reflector, and measure a spectrum from the detected light; and a processor configured to acquire a unit spectrum for a biological substance based on the spectrum measured by the spectrometer.

The biological tissue simulation solution may include at least one of gelatin, silica, intralipid, and a serum solution.

The biological tissue simulation solution may include a scatterer for scattering the light emitted by the spectrometer.

The reflector may be formed of a reflective material with a reflectance of 100%.

The spectrometer may measure the spectrum based on at least one of infrared spectroscopy and Raman spectroscopy.

The processor may be further configured to control the spectrometer to acquire a first spectrum from the receptor when the receptor contains a first biological tissue simulation solution, acquire a second spectrum from the receptor when the receptor contains a second biological tissue simulation solution, and acquire the unit spectrum based on the acquired first spectrum and second spectrum.

The first biological tissue simulation solution may not include the biological substance, and the second biological tissue simulation solution may include the biological substance.

The receptor may include an inlet configured to input the biological tissue simulation solution, a storage configured to store the biological tissue simulation solution flowing in through the inlet, and an outlet configured to discharge the biological tissue simulation solution stored in the storage.

When the first biological tissue simulation solution flows in through the inlet and then is stored in the storage, the processor may control the spectrometer to measure the first spectrum. When, after the first spectrum is measured, the second biological tissue simulation solution flows in through the inlet for a predetermined time, the first biological tissue simulation solution is discharged through the outlet, and then the second biological tissue simulation solution is stored in the storage, the processor may control the spectrometer to measure the second spectrum.

The processor may be further configured to correct at least one of a spectral intensity, an offset, and a slope of the first spectrum and the second spectrum and acquire the unit spectrum based on the corrected first spectrum and second spectrum.

The processor may estimate a light traveling path in the second biological tissue simulation solution based on a light traveling path in an aqueous solution and may acquire the unit spectrum based on the estimated light traveling path.

According to an aspect of another exemplary embodiment, there is provided a method for acquiring a unit spectrum including: emitting a first light to a storage when the storage contains a first serum solution without a bio substance; detecting the first light passing through the first serum solution and reflecting from a reflective material; emitting a second light to the storage when the storage contains a second serum solution comprising the bio substance; detecting the second light passing through the serum solution and reflecting from the reflective material; and obtaining a unit spectrum based on the detected first light and the detected second light.

The method may further include: obtaining a first spectrum from the detected first light; and obtaining a second spectrum from the detected second light. The obtaining the unit spectrum may further include subtracting the first spectrum from the second spectrum to obtain the unit spectrum.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
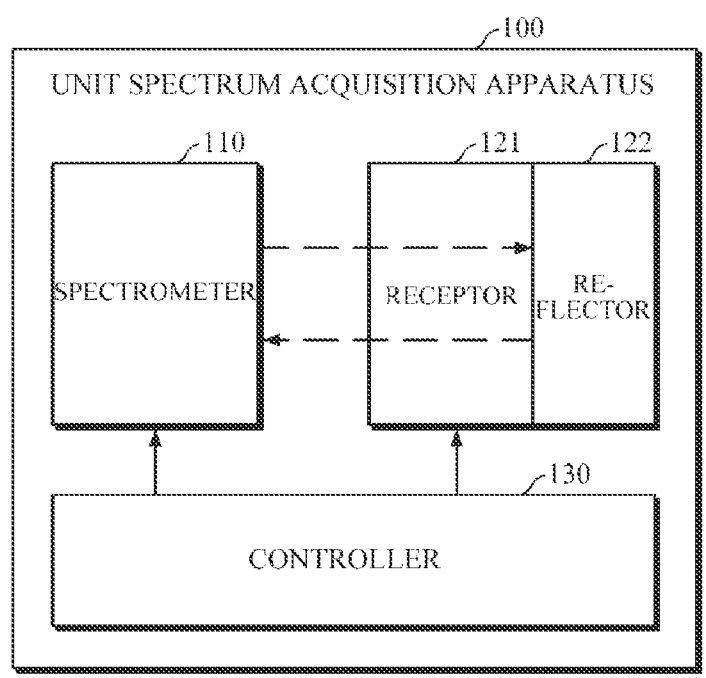
FIG. 1 is a block diagram of an apparatus for acquiring a unit spectrum according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Relational terms such as first, second, and the like may be used for describing various elements, but the elements should not be limited by the terms. The above terms are used only to distinguish one component from another. The singular forms 'a,' 'an,' and 'the' include plural reference unless the context clearly dictates otherwise. Furthermore, when one part is referred to as "comprising (or including or having)" other elements, it should be understood that it can comprise (or include or have) only those elements, or other elements as well as those elements unless specifically described otherwise. Moreover, each of the terms such as "unit" and "module" used herein denotes an element for performing at least one function or operation and may be implemented in hardware, software or a combination of hardware and software.

Expressions such as "at least one of," when preceding a list of elements, modify the entire list of elements and do not modify the individual elements of the list.

Figure 2:
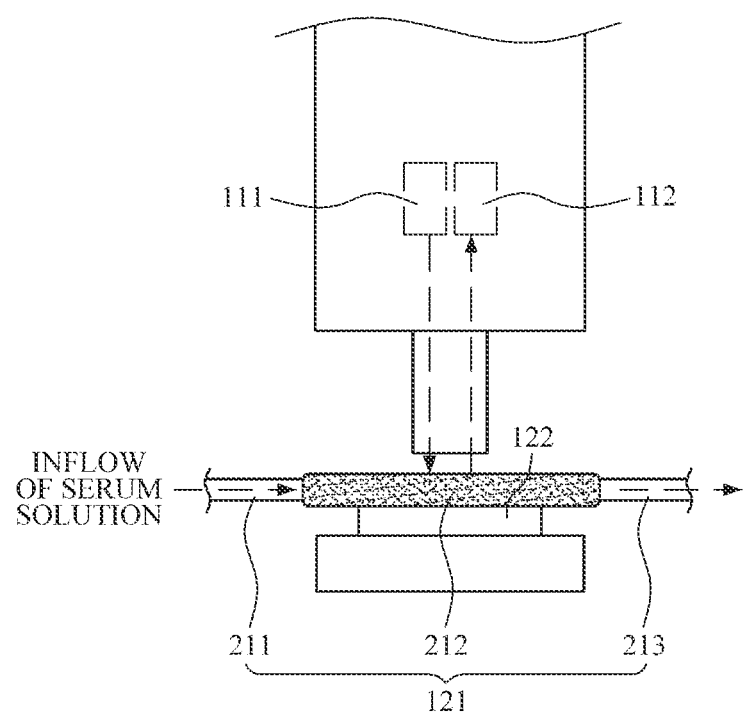
FIG. 2 is a schematic structural diagram of the unit spectrum acquisition apparatus according to the exemplary embodiment of FIG. 1.
Figure 3A:
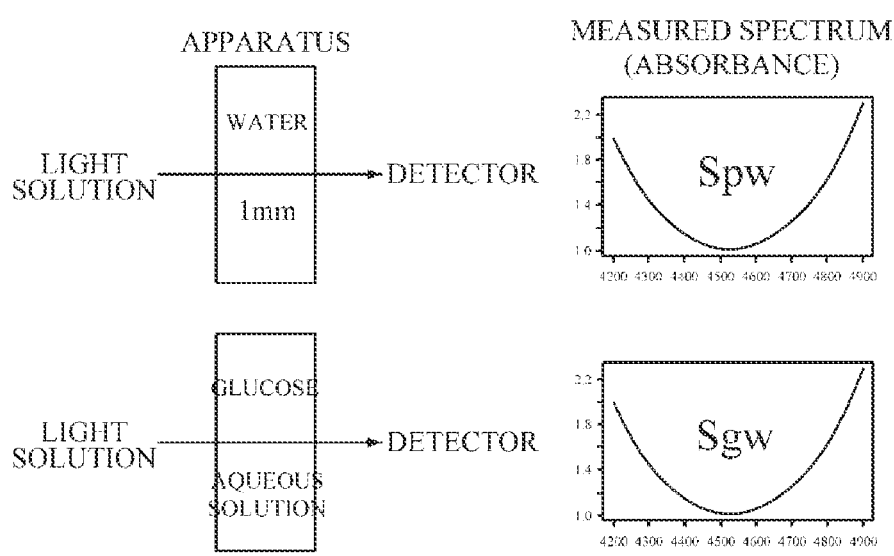
FIGS. 3A, 3B, and 3C are views for describing methods of acquiring unit spectra.
Figure 3B:
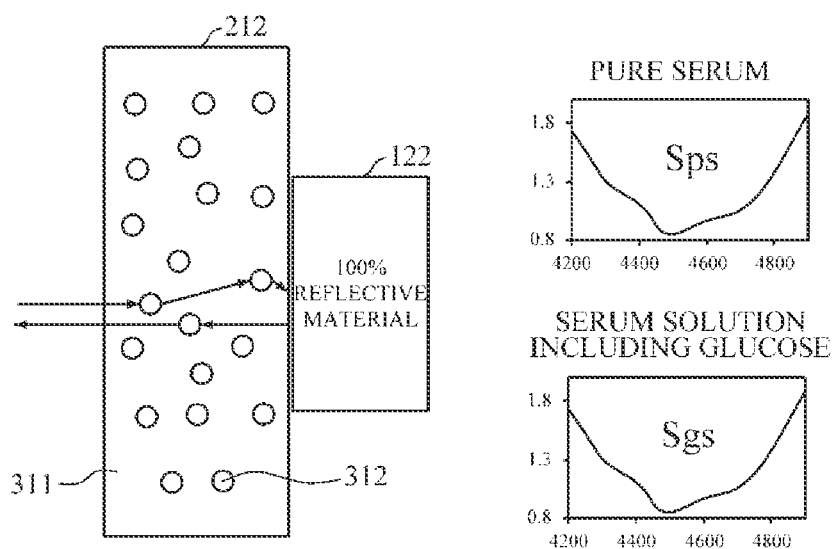
Figure 3C:
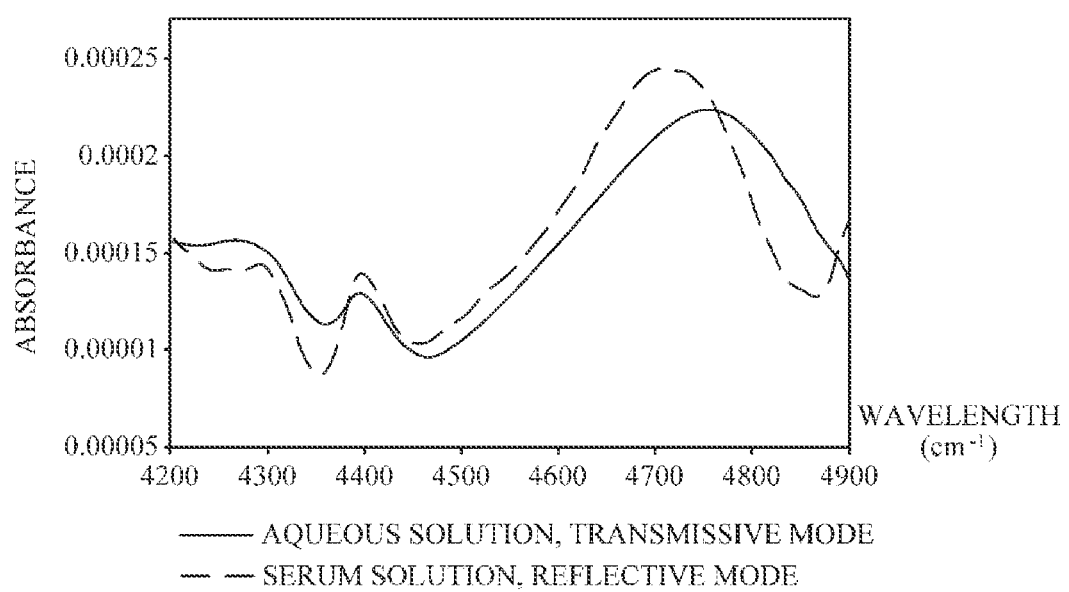

FIG. 1 is a block diagram of an apparatus for acquiring a unit spectrum according to an exemplary embodiment. FIG. 2 is a schematic structural diagram of the unit spectrum acquisition apparatus of FIG. 1. FIGS. 3A to 3C are views for describing a method of acquiring a unit spectrum.

Referring to FIG. 1, a unit spectrum acquisition apparatus 100 includes a spectrometer 110, a receptor 121, a reflector 122, and a controller 130. In this case, the controller 130 may be implemented as one or more processors, one or more memories, or a combination thereof.

Referring to FIG. 2, the spectrometer 110 may include a light source 111 configured to emit light and a detector 112 configured to detect light and acquire a spectrum. Here, the light source 111 may be configured to emit light in a near-infrared ray (NIR) band or a mid-infrared ray (MIR) band but is not limited thereto. The light source 111 may include a light-emitting diode (LED) or a laser diode. In addition, the detector 112 may include a photo diode, a photo transistor PTr, or a charge-coupled device (CCD) but is not limited thereto. The detector 112 may be implemented as one or more.

The receptor 121 accepts a solution for simulating biological tissue to acquire a unit spectrum. In this case, the biological-tissue simulation solution is a glucose serum solution similar to human skin tissue. However, exemplary embodiments are not limited thereto. A serum solution may be a serum solution acquired from an actual blood sample of a user and may be a solution including a biological substance that can be estimated in a non-invasive way, such as gelatin, silica, and intralipid. In this case, the biological-tissue simulation solution may include a scatterer such as proteins that serve to scatter light in skin tissue in order to simulate a light scattering phenomenon of biological tissue.

The reflector 122 is disposed at a rear surface of the receptor 121. When the light emitted by the light source 111 reaches the reflector 122 through the biological-tissue simulation solution, the reflector 122 reflects the light toward the detector 112. In this case, the reflector 122 may be formed of a reference material with a reflectance of 100%, for example, polytetrafluoroethylene (e.g., Teflon) or a mirror, in order to simulate a reflection phenomenon of the biological tissue.

The controller 130 may control the spectrometer 110 to acquire a spectrum from the biological tissue simulation solution of the receptor 121 and may acquire a unit spectrum of a biological substance to be estimated using the acquired spectrum. The biological substance may include a blood substance and a skin substance. The blood substance may include blood sugar, neutral fat, cholesterol, calories, proteins, uric acid, etc. In addition, the skin substance may include proteins including at least one of collagen, elastin, and keratin, body fat, etc. However, the exemplary embodiments are not limited thereto.

For convenience, the following description will be focused on an exemplary embodiment in which blood sugar is estimated as the biological substance using a glucose serum solution as the biological-tissue simulation solution.

FIG. 3A illustrates a method of acquiring a unit spectrum in a transmissive way by using a general aqueous solution. FIG. 3B illustrates a method of acquiring a unit spectrum in a reflective way by using a serum solution. FIG. 3C shows an example in which there is a difference between the unit spectrum acquired in a transmissive way using the aqueous solution of FIG. 3A and the unit spectrum acquired in a reflective way using the serum solution of FIG. 3B.

Referring to FIG. 3A, generally, an apparatus for acquiring a unit spectrum for blood sugar acquires a spectrum in a transmissive way using an aqueous solution rather than a biological tissue simulation solution. For example, a related-art apparatus emits light into a container containing pure water and detects light transmitted through the container to measure a spectrum Spw. Next, the related-art apparatus emits light into a container containing an aqueous solution including sugar and detects light transmitted through the container to measure a spectrum Sgw. In turn, the related-art apparatus acquires a unit spectrum Su by subtracting the spectrum Spw measured from the pure aqueous solution from the spectrum Sgw measured from the aqueous solution including sugar. Here, Cg denotes a sugar concentration.

$$Su = \frac{Sgw - Spw}{Cg} \quad\quad \text{[Equation 1]}$$

However, since reflection, diffraction, and scattering of light that occur in biological tissue are not considered in the unit spectrum for the blood sugar acquired in a transmissive way using the aqueous solution, there are limitations to accurately expressing a signal of blood sugar that exists in skin.

According to an exemplary embodiment, as shown in FIG. 3B, a unit spectrum may be acquired in a similar way to the biological tissue. For example, light may be emitted to a storage 121 of the receptor 121, which contains a serum solution 311 including a scatterer 312, and acquire the unit spectrum based on the light scattered and diffracted from the scatterer 312 and the light reflected from the reflector 122.

Referring to FIG. 2, the receptor 121 may include an inlet 211, a storage 212, and an outlet 213. Generally, when the receptor 121, which contains a solution, is replaced in order to measure a unit spectrum, distance and angle between a light source and a sample may vary, and thus the light source and the sample may be misaligned, making it difficult to accurately measure a spectrum. To this end, according to an exemplary embodiment, the serum solution may be stored in the storage 212 in a manner in which the serum solution flows through the inlet 211 for a predetermined time while the receptor 121 is fixed.

For example, the controller 130 may control a first serum solution 311, which does not include sugar, to flow into the storage 212 through the inlet 211 of the receptor 121 for a predetermined time. After the predetermined time, when the first serum solution 311 becomes stored in the storage 212, the controller 130 may control the spectrometer 110 to acquire a spectrum Sps of the first serum solution. Next, the controller 130 controls a second serum solution, which includes sugar, to flow into the storage 212 through the inlet 211 for a predetermined time while the receptor 121 is fixed. After the predetermined time, when the first serum solution that was stored in the storage 212 is discharged through the outlet 213 and the second serum solution becomes stored, the controller 130 may control the spectrometer 110 to acquire a spectrum Sgs of the second serum solution. The controller 130 may use the spectrum Sps of the first serum solution and the spectrum Sgs of the second serum solution to acquire a unit spectrum for blood sugar.

A slope, an offset, and a spectral intensity of a spectral waveform, an intensity of a spectrum may vary depending on a temperature difference and a measurement environment of a point when the spectrum is measured. In consideration of this, when the spectra Sps and Sgs are acquired from the first serum solution and the second serum solution, the controller 130 may correct spectrum intensities, offsets, or slopes of the acquired spectra Sps and Sgs using a reference spectrum that is measured using a serum solution in a standard state.

In addition, since the spectral intensity varies along a light traveling path, the controller 130 may estimate a light traveling path in the serum solution and may acquire the unit spectrum based on the estimated light traveling path. For example, since 91% of the serum solution is water, the controller 130 may estimate the light traveling path in the serum solution by converting the spectral intensity acquired on the basis of the light traveling path in the aqueous solution.

When all of the spectrum Sps of the first serum solution, the spectrum Sgs of the second serum solution, and the light traveling path L are acquired, the controller 130 may acquire the unit spectrum Su using Equation 2 below. Here, when corrected, the spectrum Sps of the first serum solution and the spectrum Sgs of the second serum solution are obtained after the correction. Cg denotes a sugar concentration.

$$Su = \frac{Sgs - Sps}{Cg \times L} \quad \text{[Equation 2]}$$

Figure 4:
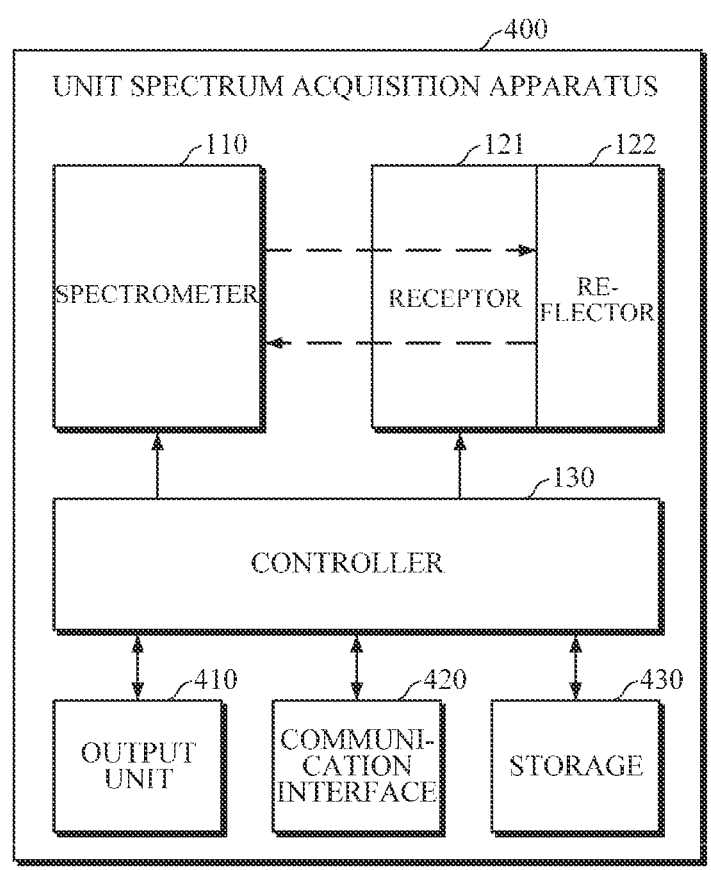
FIG. 4 is a block diagram of a unit spectrum acquisition apparatus according to another exemplary embodiment.

FIG. 4 is a block diagram of a unit spectrum acquisition apparatus according to another exemplary embodiment.

Referring to FIG. 4, a unit spectrum acquisition apparatus 400 may include a spectrometer 110, a receptor 121, a reflector 122, a controller 130, an output unit 410, a communication interface 420, and a storage 430.

The spectrometer 110, the receptor 121, reflector 122, and the controller 130 have been described above, and thus detail descriptions thereof will be omitted.

The output unit 410 may provide the acquired unit spectrum to a user in various ways, for example, in a visual or non-visual way under the control of the controller 130. For example, the output unit 410 may include a display device, a speaker, a haptic device, etc. but is not limited thereto.

The communication interface 420 communicates with an external device in a wired or wireless manner to transmit or receive data regarding the unit spectrum. For example, the communication interface 420 may include one or more modules that perform Bluetooth communication, Bluetooth low energy (BLE) communication, near field communication, wireless LAN (WLAN) communication, Zigbee communication, Infrared Data Association (IrDA) communication, Wi-Fi Direct (WFD) communication, ultra wideband (UWB) communication, Ant+ communication, WiFi communication, 3G communication, 4G communication, 5G communication, or the like.

The controller 130 may receive a request to provide a unit spectrum from an external device through the communication interface 420. When the unit spectrum is acquired, the controller 130 controls the communication interface 420 to transmit the unit spectrum to the device that has requested the unit spectrum.

The storage 430 may manage the acquired unit spectrum and various pieces of associated information. The storage 430 may manage information such as the unit spectrum for each user and also may manage the change in the unit spectrum for each user. The storage 430 may include a flash memory type memory, a hard disk type memory, a multimedia card micro type memory, a card type memory (e.g., an SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc. However, embodiments of the present disclosure are not limited thereto.

The unit spectrum acquisition apparatus 100 or 400 according to the above-disclosed embodiment may be installed in a medical institution and may measure and update a unit spectrum to be utilized to estimate blood sugar of a diabetic patient or a user who needs blood sugar management. In addition, the unit spectrum acquisition apparatus 100 or 400 may acquire a unit spectrum that may accurately consider a blood sugar signal of a user who regularly visits a medical examination center by extracting a serum solution from a blood sample of the user and utilizing the serum solution of the user to acquire the unit spectrum. However, an installation place, a size, or an installation method of the unit spectrum acquisition apparatus 100 or 400 is not limited and may be changed variously depending on the purpose of use.

Figure 5:
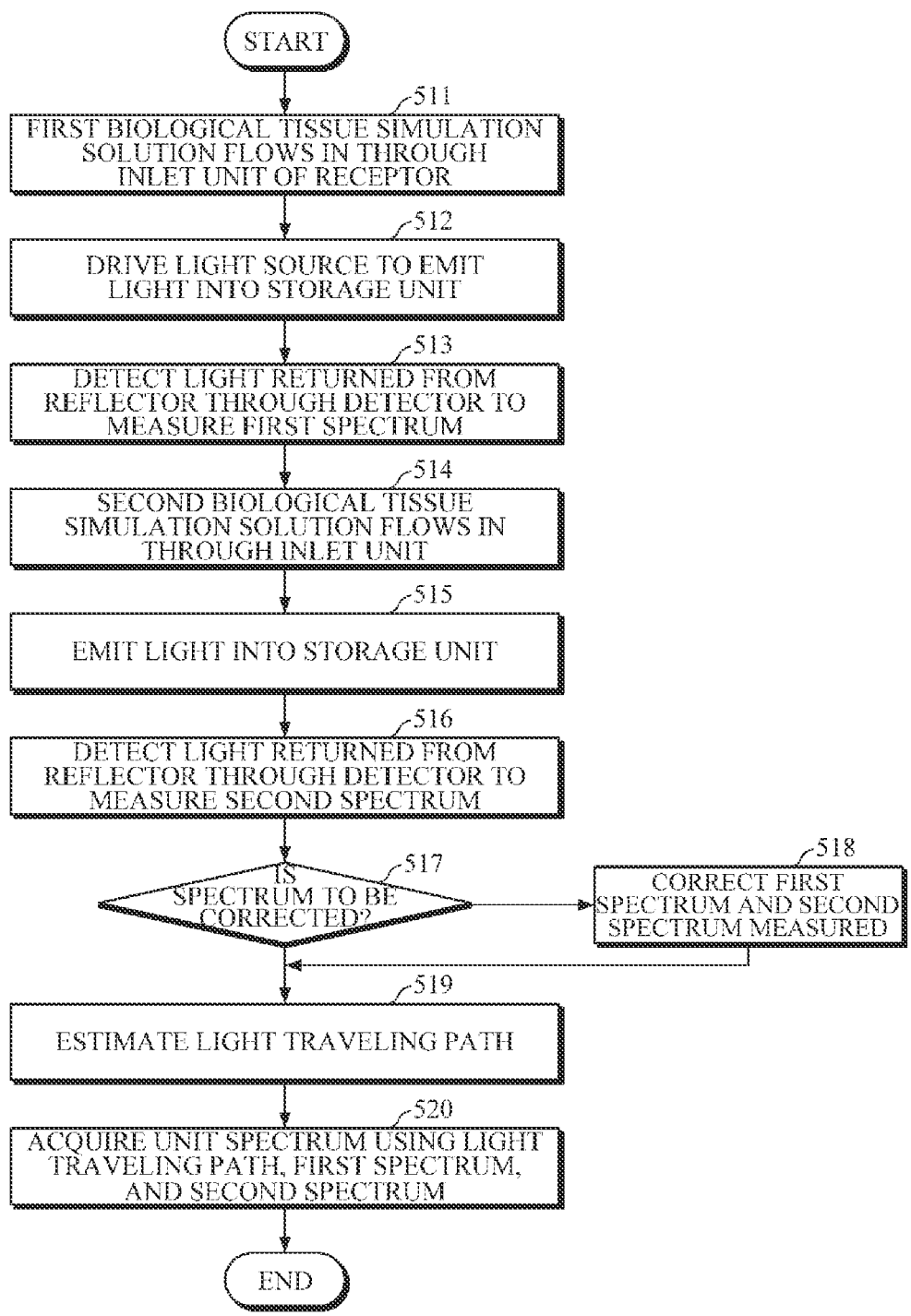
FIG. 5 is a flowchart of a method of acquiring a unit spectrum according to an exemplary embodiment.

FIG. 5 is a flowchart of a method of acquiring a unit spectrum according to an exemplary embodiment.

The method of FIG. 5 may be performed by the unit spectrum acquisition apparatus 100 or 400.

First, a first biological tissue simulation solution is allowed to flow into a storage through an inlet of a receptor (operation 511). Here, the first biological tissue simulation solution may be a serum solution that does not include a biological substance (e.g., sugar) to be estimated. The serum solution may be a glucose serum solution and include a scatterer that may generate light scattering or diffraction phenomenon, similarly to human skin tissue. However, the exemplary embodiments are not limited thereto. The first biological tissue simulation solution may include a solution such as gelatin, silica, and intralipid in which the biological substance to be estimated is not included.

Next, when the first biological tissue simulation solution is contained in the storage, a light source is driven to emit light into the storage (operation 512). Here, the light source may emit light in a near-infrared (NIR) band or a mid infrared (MIR) band but is not limited thereto. The light source may be configured to emit single-wavelength laser light.

Next, light returned from the storage is detected through a detector to measure a first spectrum (operation 513). In this case, the detector may include one or more photodiodes. The light emitted into the first biological tissue simulation solution of the storage is scattered or diffracted by the scatterer, reflected, and then returned by the reflector, similarly to the skin tissue. The returned light is detected by the detector.

Next, when the first spectrum is measured, a second biological tissue simulation solution is allowed to flow into the storage through the inlet (operation 514). As the second biological tissue simulation solution flows into the storage for a predetermined time, the first biological tissue simulation solution is discharged through an outlet, and the second biological tissue simulation solution is placed in the storage. Here, the second biological tissue simulation solution may be a serum solution that includes a biological substance (e.g., sugar) to be estimated and may include a scatterer such as protein. Likewise, the second biological tissue simulation solution may include a solution such as gelatin, silica, and intralipid in which the biological substance to be estimated is included.

Next, the light source is driven to emit light into the storage (operation 515). The light that is reflected by the reflector or scattered or diffracted by the scatter and then returned is detected for measuring a second spectrum (operation 516).

Next, it may be determined whether the measured first and second spectra need to be corrected (operation 517). In this case, whether one or more of a slope, an offset, and a spectral intensity of a spectral waveform need to be corrected may be determined on the basis of a reference spectrum measured in a standard state. Generally, the slope or offset of the spectral waveform may vary depending on a location of an object of which spectrum is to be measured, a temperature upon the measurement, etc.

Next, when it is determined in operation 517 that the correction is needed, the slop, the offset, and the intensity of the measured first spectrum and second spectrum may be corrected (operation 518).

Next, in order to reflect that the spectral intensity changes along a light traveling path, a light traveling path in the second biological tissue simulation solution may be estimated (operation 519). For example, generally, since 91% of the serum solution is water, the light traveling path in the serum solution may be estimated by converting the spectrum intensity on the basis of the light traveling path in water.

Next, a unit spectrum for the biological substance may be acquired using the estimated light traveling path and the measured first spectrum and second spectrum (operation 520). As an example, the unit spectrum may be calculated using Equation 2 above.

Figure 6:
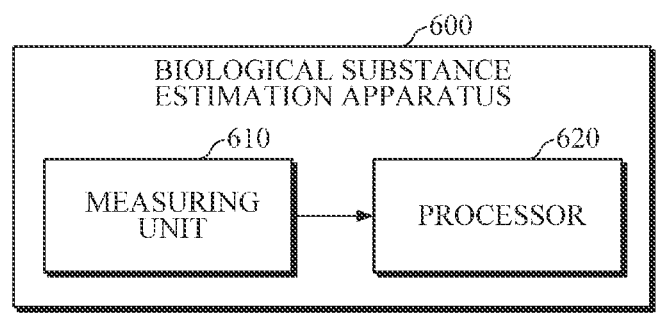
FIG. 6 is a block diagram of an apparatus for estimating a biological substance.

FIG. 6 is a block diagram of an apparatus for estimating a biological substance according to an exemplary embodiment. A biological substance estimation apparatus 600 according to an exemplary embodiment may be mounted on a device wearable by a user. Here, the wearable device includes a watch type, a wristlet type, a wrist band type, a ring type, a glasses type, and a hair band type and is not limited in shape or size.

Referring to FIG. 6, the biological substance estimation apparatus 600 includes a measuring unit 610 and a processor 620. The measuring unit 610 may be implemented by the combination of a light emitter and a light receiver, and/or a spectrometer.

The measuring unit 610 measures a spectrum from the user's skin. The measuring unit 610 may emit the user's skin with light according to a predetermined control signal and detect light returned from the skin to measure the spectrum. When the spectrum is measured from the user's skin, the measuring unit 610 may deliver data on the measured spectrum to the processor 620, thus allowing the processor 620 to perform a process needed to estimate the biological substance. Here, the measuring unit 610 may use Infrared spectroscopy or Raman spectroscopy but is not limited thereto. The measuring unit 610 may measure the spectrum by utilizing various spectroscopies.

The processor 620 may analyze the spectrum data and process various operations associated with the biological substance in the user. The processor 620 may be implemented by one or more circuits, one or more processors, one or more memories, or a combination thereof. Here, the biological substance may include one or both of a blood substance and a skin substance. Here, the blood substance may include one or more of blood sugar, cholesterol, neutral fat, proteins, and uric acid, and the skin substance may include one or both of body fat and proteins including at least one of collagen, elastin, and keratin. However, the exemplary embodiments are not limited thereto. For convenience, the following description will use the blood sugar as an example.

When the skin spectrum for estimating the biological substance is measured by the measuring unit 610, the processor 620 may estimate the biological substance in the user on the basis of the measured skin spectrum and the unit spectrum.

For example, when a skin spectrum for estimating blood sugar is acquired, the processor 620 may calculate a predicted blood sugar value using Equation 3 below. Referring to Equation 3, when the skin spectrum Sm for estimating the blood sugar is acquired, the processor 620 may remove noise caused by a skin component by subtracting a background spectrum Sb from the skin spectrum Sm in order to increase a signal-to-noise ratio (SNR). Here, the background spectrum Sb may be a spectrum that is repetitively measured in a reference state (e.g., a fasting state) at certain intervals for a certain time. Here, the reference state may be defined differently for each user according to the user's characteristics.

In addition, the processor 620 may calculate an estimated blood sugar value $$\frac{BS}{Su}.$$

on the basis of the unit spectrum Su and a blood sugar signal BS from which noise has been removed and may calculate a final predicted blood sugar value BG by adding a reference blood sugar value RG to the calculated estimated blood sugar value $$\frac{BS}{Su}$$

$$BS = Sm - Sb \qquad \text{[Equation 3]}$$
$$BG = RG + \frac{BS}{Su}$$

Here, the unit spectrum may be acquired using a biological-tissue simulation solution by the unit spectrum acquisition apparatus 100 or 400 that has been described above and may be input in advance to the biological substance estimation apparatus 600. As described above, the unit spectrum is measured using a solution similar to human skin tissue that is irradiated with light in order to estimate the biological substance, thus more accurately reflecting the user's biological substance, for example, a signal for blood sugar.

Figure 7:
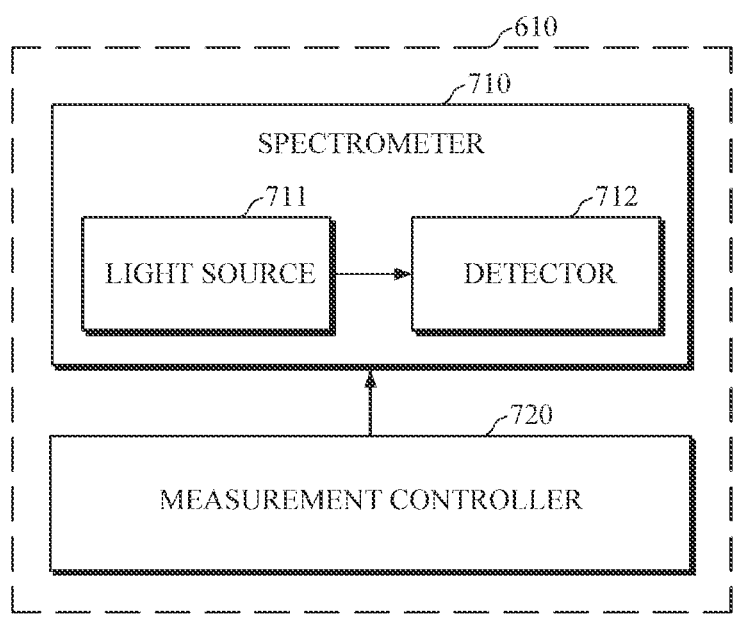
FIG. 7 is a block diagram showing an example of a measuring unit of FIG. 6.

FIG. 7 is a block diagram showing an example of the measuring unit 610 of FIG. 6.

Referring to FIG. 7, the measuring unit 610 may include a spectrometer 710 and a measurement control unit 720.

The spectrometer 710 may include a light source 711 configured to emit light to a user's skin and a detector 712 configured to detect the light scattered by or reflected from the skin and then returned to the spectrometer 710 and measure a skin spectrum from the detected light.

The light emitted from the light source 711 may have wavelengths in an NIR band or an MIR band but is not limited thereto. The light emitted by the light source 711 reaches biological tissue via the user's skin. The light that has reached the biological tissue is returned via the user's skin. The detector 712 may detect the light returned via the user's skin to obtain a spectrum. The detector 712 may be formed with an indium gallium arsenide (InGaAs) photodiode and may be formed with one or more.

Here, the user's skin irradiated with light may be an area adjacent to the radial artery of the wrist. A skin area in which the radial artery is found may be less affected by external factors that generate measurement error such as thickness of skin tissue of the wrist. However, the exemplary embodiments are not limited thereto. The user's skin irradiated with light may be a human peripheral part such as a finger, a toe, or an earlobe, for which a vascular density is high.

The measurement controller 720 may generate a control signal according to the user's command or a preset criterion to control the spectrometer 710.

As an example, the measurement controller 720 may be connected with a manipulation unit of a health care device equipped with the biological substance estimation apparatus 600. The measurement controller 720 may receive a spectrum measurement command that is input by the user through the manipulation unit and generate a control signal for controlling the spectrometer 710. Here, the spectrum measurement command may be a command for measuring a skin spectrum for estimating a biological substance or a command for measuring a background spectrum for removing noise.

As another example, a measurement criterion for the skin spectrum or the background spectrum may be preset, and the measurement controller 720 may automatically generate a control signal according to the preset measurement criterion to control the spectrometer 710.

For example, for a user whose blood sugar management is very important, such as a diabetic patient, blood sugar estimation time may be preset to perform blood sugar estimation at certain time in order to regularly estimate blood sugar in a fasting state or blood sugar after a meal. For example, the spectrometer 710 may be set to measure a skin spectrum at 7:00 a.m. daily in order to estimate the fasting state blood sugar and may be set to measure a spectrum at 13:00 p.m. for a user who regularly eats lunch at 12:00 p.m.

In addition, a calibration cycle of a background spectrum that is measured for removing noise of the measured skin spectrum may be preset. For example, the calibration cycle of the background spectrum may be set to be performed every minute for 30 minutes from 7:00 a.m. on a specific day of the week every week after the user is registered for the first time to use the biological substance estimation apparatus 600. However, the exemplary embodiments are not limited thereto. The number, cycles, or time intervals of measurements may be variously adjusted on the basis of a measurement purpose, measurement accuracy, a measurement location, a user's life pattern, etc.

The measurement controller 720 has been described as an element of the measuring unit 610 but is not limited thereto. The measurement controller 720 may be implemented as an element of the processor 620. In some cases, alternatively, the measurement controller 720 may be implemented as a separate module.

Figure 8:
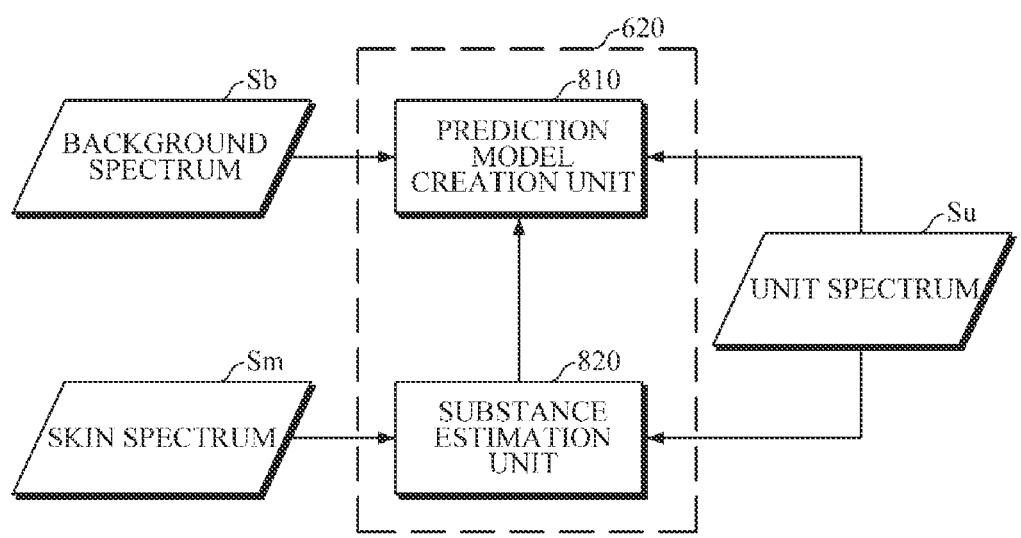
FIG. 8 is a block diagram showing an example of a processor of FIG. 6.

FIG. 8 is a block diagram showing an example of the processor 620 of FIG. 6.

Referring to FIG. 8, the processor 620 may include a prediction model creation unit 810 and a substance estimation unit 820.

The prediction model creation unit 810 may create a prediction model to be applied to estimate a biological substance. When a background spectrum Sb is received from the measuring unit 610, the prediction model creation unit 810 may set the received background spectrum Sb as learning data. Here, the background spectrum Sb may be measured by the measuring unit 610 in a calibration cycle and delivered, and the prediction model creation unit 810 may reset the learning data whenever the background spectrum Sb is received. In addition, the prediction model creation unit 810 may create a prediction model needed to estimate a biological substance using the learning data or update an existing prediction model.

For example, the prediction model creation unit 810 may create an equation for blood sugar estimation, such as Equation 4 below, as the prediction model using the Beer Lambert's law. However, the blood sugar estimation equation of Equation 4 is merely an example and is not limited thereto.

$$S_m = [S_{b1} + S_{b2} + S_{b3} + S_{b4} + \ldots] + \varepsilon_g \cdot L \cdot C_g \quad \text{[Equation 4]}$$

Here, Sm is a user's skin spectrum measured to estimate blood sugar, and $[S_{b1}+S_{b2}+S_{b3}+S_{b4}+ \ldots]$ is learning data that is set using a background spectrum measured for a predetermined time. εg is a coefficient for a unit spectrum Su for blood sugar, and L is a light traveling path in a serum solution in which the unit spectrum Su is measured. As described above, the unit spectrum coefficient and the light traveling path may be acquired using a serum solution by the unit spectrum acquisition apparatus and may be input in advance to the biological substance estimation apparatus 600. In addition, Cg is an estimated blood sugar value needed to calculate a predicted blood sugar value of a user.

When the skin spectrum Sm for estimating blood sugar is delivered from the measuring unit 610, the substance estimation unit 820 may apply the skin spectrum Sm to the prediction model created using Equation 4 to calculate an estimated blood sugar value Cg and may add a reference blood sugar value, for example, fasting blood sugar of a user to the estimated blood sugar value Cg, to estimate a final blood sugar value.

Figure 9:
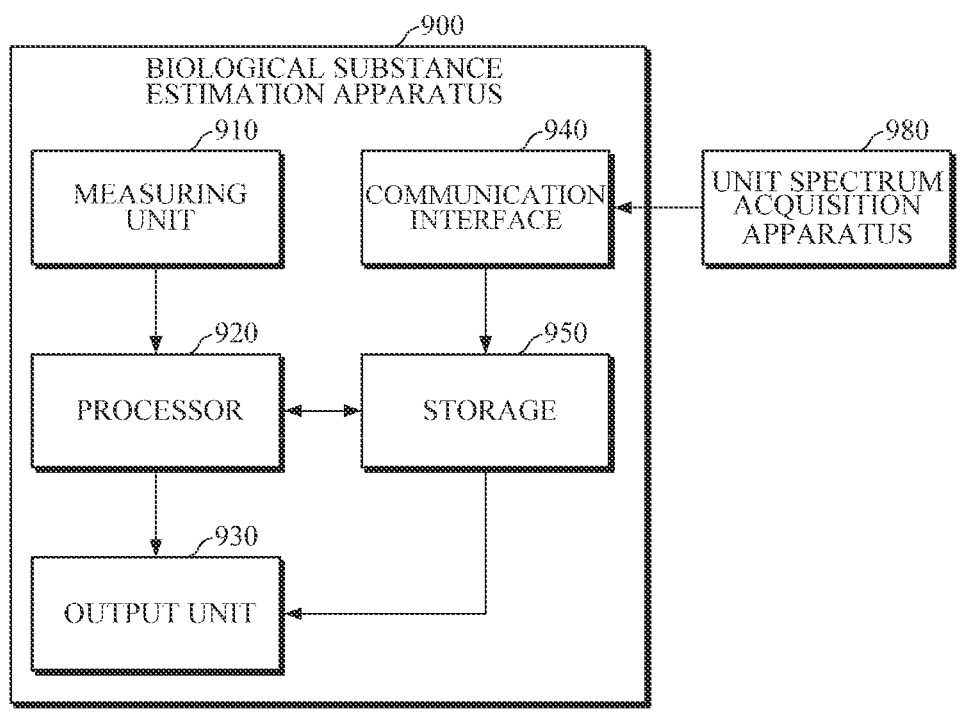
FIG. 9 is a block diagram of an apparatus for estimating a biological substance according to another exemplary embodiment.

FIG. 9 is a block diagram of an apparatus for estimating a biological substance according to another exemplary embodiment.

Referring to FIG. 9, the biological substance estimation apparatus 900 may include a measuring unit 910, a processor 920, an output unit 930, a communication interface 940, and a storage 950. The measuring unit 910 and the processor 920 may perform substantially the same functions as the measuring unit 610 and the processor that have been described with reference to FIGS. 6 to 8, and thus detail description thereof will be omitted.

The output unit 930 may output a processed result, warning information, or alarm information of the processor 920 in a visual or non-visual manner. For example, according to an output criteria stored in the storage 950, the output unit 930 may perform the output operation using color, vibration, or voice corresponding to a range (e.g., normal or excessive) of the estimated blood sugar value and also may output an alarm or a warning. Here, the output unit 930 may be a display device, a speaker, or a haptic device or may include an output transmitter, etc.

The communication interface 940 may include the above-described communication modules and may be communicatively connected with the unit spectrum acquisition apparatus 980 and an external device such as a mobile terminal possessed by a user to transmit or receive necessary data. Here, the external device may include mobile terminals such as a smartphone, a tablet PC, and a mobile communication terminal or a desktop, a notebook, a laptop, etc.

As an example, the communication interface 940 may receive a unit spectrum from the unit spectrum acquisition apparatus 980. For example, when a user with diabetes mellitus has his/her blood collected in a hospital to take a medical examination, a unit spectrum acquisition apparatus installed in the hospital may acquire a unit spectrum from a blood sample collected from the user and deliver the acquired unit spectrum to the communication interface 940. The communication interface 940 may receive the unit spectrum from the unit spectrum acquisition apparatus 980, and the storage 950 may store and manage the received unit spectrum.

As another example, the communication interface 940 may transmit the processed result of the processor 920 to an external device that has higher computing performance than the biological substance estimation apparatus 900 such that information regarding the biological substance may be managed and provided to the user through the external device in various ways.

The storage 950 may store the processed results of the processor 920, for example, an estimated result and a prediction model of the biological substance. The storage 950 may store the unit spectrum information received by the communication interface 940. In addition, the communication interface 940 may store information on various criteria needed to estimate the biological substance. For example, the reference information may include spectrum-measurement-associated reference information such as a calibration cycle of the background spectrum or an estimated cycle of the biological substance, user characteristic information such as age, gender, health state, and disease of a user, and output reference information such as an output method, output color corresponding to a value of an estimated biological substance, a vibration number or intensity, and alarm or warning information. However, the exemplary embodiments are not limited thereto. Various criteria may be set.

Figure 10:
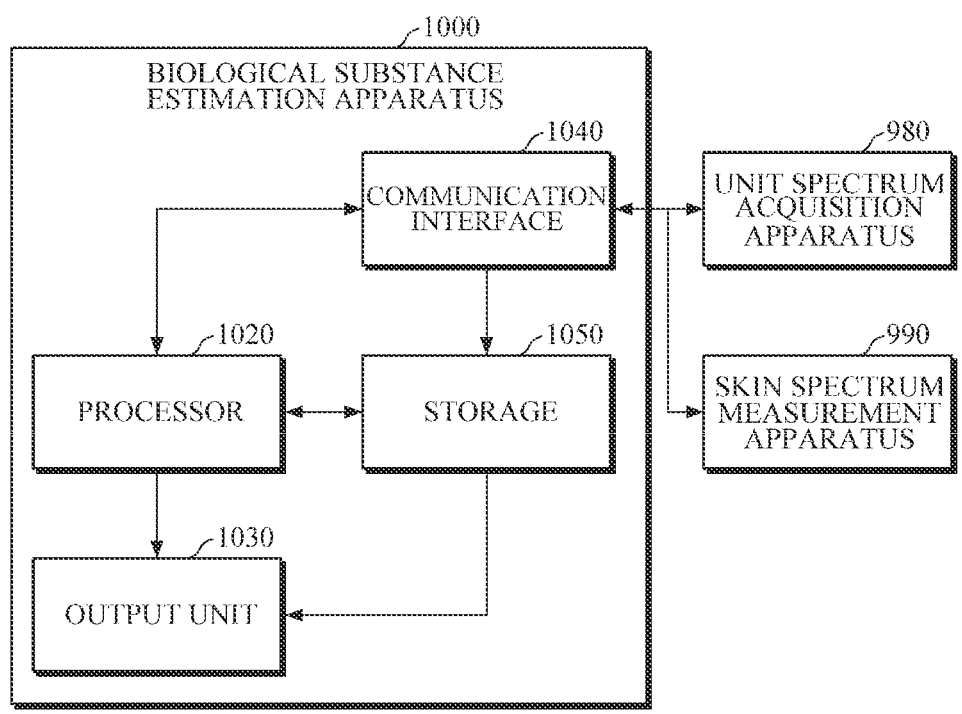
FIG. 10 is a block diagram of an apparatus for estimating a biological substance according to still another exemplary embodiment.

FIG. 10 is a block diagram of an apparatus for estimating a biological substance according to another exemplary embodiment.

Referring to FIG. 10, a biological substance estimation apparatus 1000 may include a processor 1020, an output unit 1030, a communication interface 1040, and a storage 1050. The biological substance estimation apparatus 1000 according to an exemplary embodiment may be implemented in a mobile terminal without a measuring unit and may acquire spectrum data from an external skin spectrum measurement apparatus 990.

For example, when a user enters a biological substance estimation command using an input means of a mobile terminal, the processor 1020 may receive the biological substance estimation command to control the communication interface 1040. Under the control of the processor 1020, the communication interface 1040 may be communicatively connected with a skin spectrum measurement apparatus 1200 to transmit a control signal for requesting spectrum measurement. Here, the skin spectrum measurement apparatus 990 may be a wearable device including a spectrometer. In addition, the user controls the skin spectrum measurement apparatus 990 to measure a skin spectrum and then transmit data of the measured skin spectrum data to the biological substance estimation apparatus 1000 to request the biological substance estimation apparatus 1000 to estimate a biological substance.

The output unit 1030 may output a result of estimating the biological substance by the processor 1020 in a visual or non-visual manner according to output criterion information stored in the storage 1050.

The communication interface 1040 may communicate with the unit spectrum acquisition apparatus 980 or the skin spectrum measurement apparatus 990 using the above-described communication scheme to receive unit spectrum data or skin spectrum data. In addition, when the skin spectrum measurement apparatus 990 includes an output module, the communication interface 1040 may transmit the processed result of the processor 1020 to the skin spectrum measurement apparatus 990 to output the processed result.

As described above, the storage 1050 may manage the processed result of the processor 1020, various kinds of warning or alarm information, various pieces of criterion information, etc.

According to an exemplary embodiment, a wearable device may be miniaturized to have only a spectrum measurement function by installing a function of estimating various biological substances from the spectrum data in a mobile terminal, thus enhancing mobile convenience.

Figure 11:
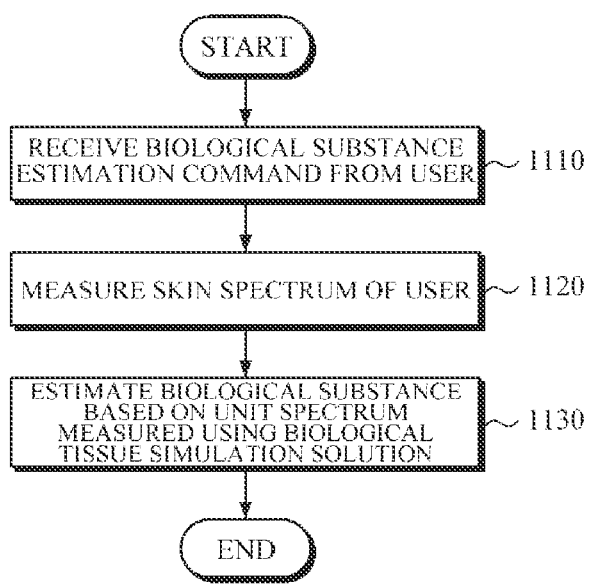
FIG. 11 is a flowchart of a method of estimating a biological substance according to an exemplary embodiment.

FIG. 11 is a flowchart of a method of estimating a biological substance according to an exemplary embodiment.

FIG. 11 shows an example of a biological substance estimation method performed by the biological substance estimation apparatus 600 according to the exemplary embodiment of FIG. 6. Various examples of the biological substance estimation method have been described in detail with reference to FIGS. 6 to 8, and thus descriptions thereof will be briefly provided to avoid redundant description.

First, the biological substance estimation apparatus 600 receives a command to estimate a biological substance from a user (operation 1110) and measures a spectrum from the user's skin. The biological substance estimation apparatus 600 may emit light to the user's skin and detect the light returned from the skin to measure a skin spectrum from the detected light. In this case, Infrared spectroscopy or Raman spectroscopy may be utilized. However, the exemplary embodiments are not limited thereto.

Next, when the skin spectrum of the user is measured, the biological substance estimation apparatus 600 may estimate a biological substance using a unit spectrum for the biological substance acquired using a biological tissue simulation solution. Here, the unit spectrum may be measured in advance in a reflective way using a solution including a scatterer such as proteins by the unit spectrum acquisition apparatus and may be input to the biological substance estimation apparatus 600.

Figure 12:
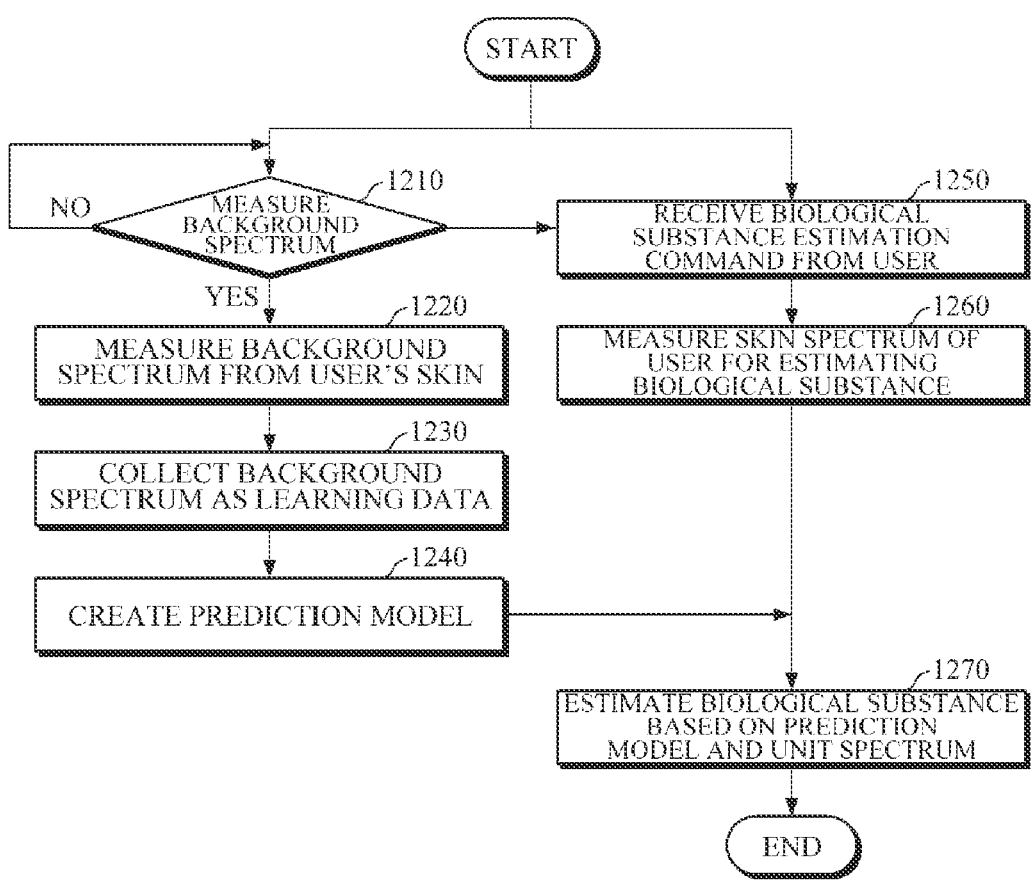
FIG. 12 is a flowchart of a method of estimating a biological substance according to another exemplary embodiment.

FIG. 12 is a flowchart of a method of estimating a biological substance according to another exemplary embodiment. A biological substance estimation method performed by the biological substance estimation apparatus 600 according to another exemplary embodiment will be described with reference to FIG. 12. First, the biological substance estimation apparatus 600 may determine whether to measure a background spectrum (operation 1210). Here, the background spectrum may be used to remove noise caused by substances other than a biological substance to be estimated from the skin spectrum measured to estimate the biological substance. When a user is registered for the first time to use the apparatus 600 or when a preset calibration cycle of the background spectrum starts, the biological substance estimation apparatus 600 may determine that a background spectrum needs to be measured. In this case, when the biological substance estimation apparatus 600 determines that background spectrum needs to be measured, the biological substance estimation apparatus 600 may inform the user that the background spectrum should be measured in a reference state, for example, in a fasting state.

Next, when the reference state is reached, the biological substance estimation apparatus 600 may emit light to the user's skin at certain intervals for a certain time and measure the background spectrum (operation 1220).

Next, when the background spectrum is measured (operation 1220), the biological substance estimation apparatus 600 may collect the measured background spectrum as learning data (operation 1230) and may create a prediction model for estimating a biological substance using the learning data (operation 1240). Here, the prediction model may be expressed as an equation for estimating a blood substance, for example, the blood sugar estimation equation illustrated as Equation 4.

Next, the biological substance estimation apparatus 600 may receive a command to estimate the biological substance from a user (operation 1250) and may measure a spectrum for estimating the biological substance from the user's skin (operation 1260).

Next, the biological substance estimation apparatus 600 may estimate the biological substance on the basis of the prediction model created in operation 1240 and the unit spectrum acquired using the biological tissue simulation solution (operation 1270).

Figure 13:
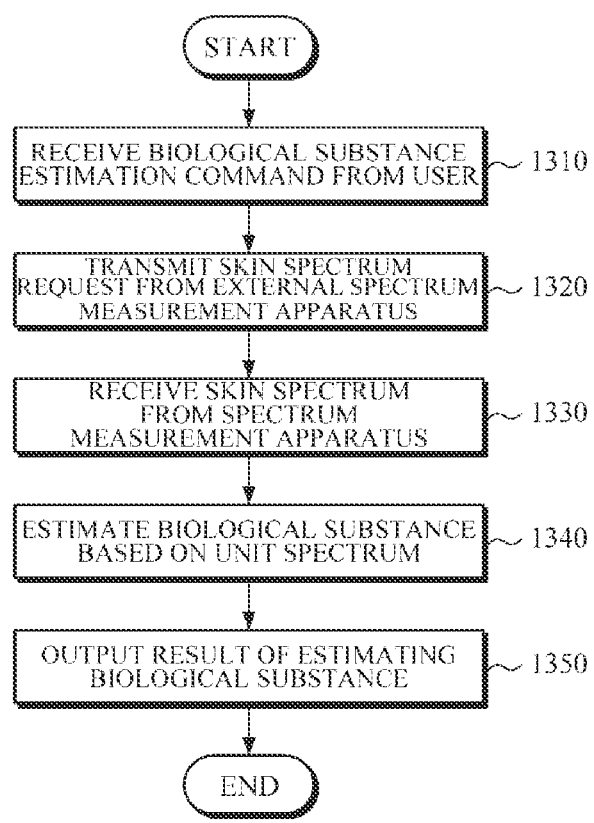
FIG. 13 is a flowchart of a method of estimating a biological substance according to another exemplary embodiment.

FIG. 13 is a flowchart of a method of estimating a biological substance according to another exemplary embodiment. The biological substance estimation method shown in FIG. 13 may be performed by the biological substance estimation apparatus 1000 according to the exemplary embodiment of FIG. 10.

First, when a command to estimate a biological substance is received from a user (operation 1310), the biological substance estimation apparatus 1000 may transmit a request to measure a skin spectrum to an external spectrum measurement apparatus (operation 1320). The spectrum measurement apparatus may be a wearable device including a spectrometer. When the spectrum measurement request is received from the biological substance estimation apparatus 1000, the spectrum measurement apparatus may emit light to the user's skin to acquire a skin spectrum and may transmit the acquired skin spectrum to the biological substance estimation apparatus 1000.

Next, the biological substance estimation apparatus 1000 may receive the skin spectrum of the user from the spectrum measurement apparatus (operation 1330) and may estimate the biological substance on the basis of a unit spectrum that is input in advance (operation 1340). When the prediction model as shown in Equation 4 is created, the biological substance estimation apparatus 1000 may apply the received skin spectrum and the unit spectrum to the prediction model to calculate a predicted value of a final blood substance.

Next, the biological substance estimation apparatus 1000 may output a result of estimating the biological substance to the user (operation 1350). Here, the result of estimating the biological substance may include a final predicted biological substance value and alarm or warning information and may be output to the user using various output means.

Figure 14:
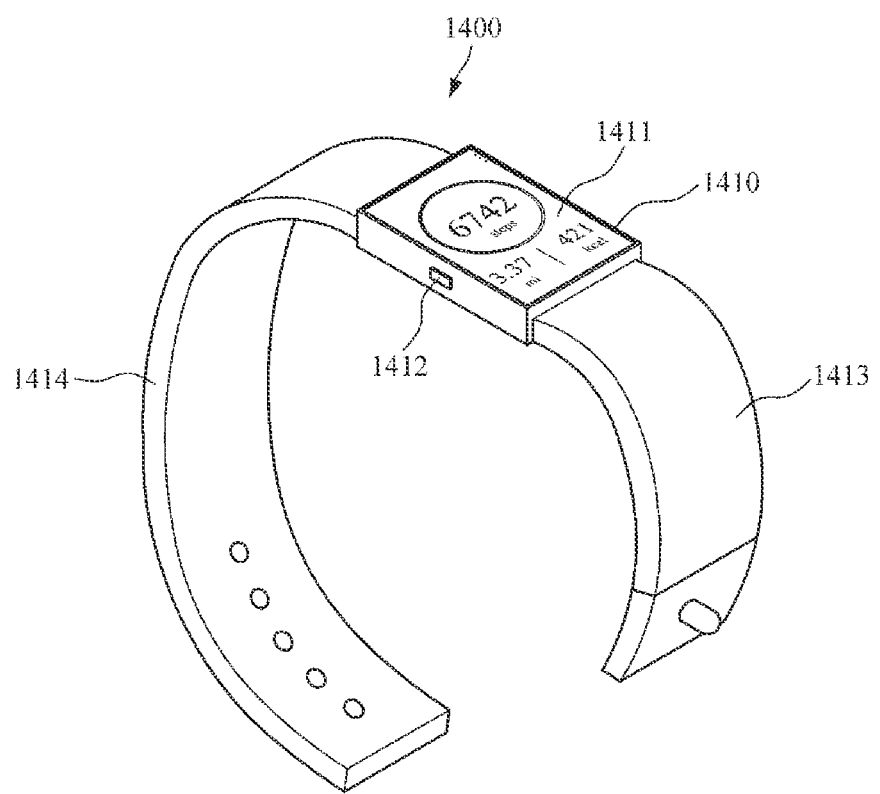
FIG. 14 is a perspective view of a wearable device according to an exemplary embodiment.
Figure 15:
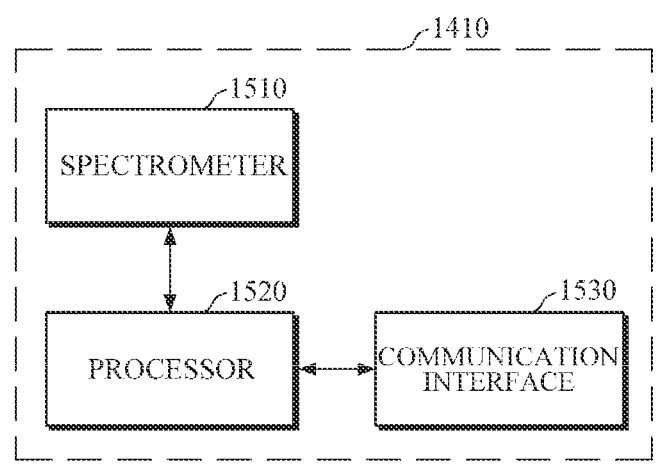
FIG. 15 is a block diagram showing elements installed in the main body of a wearable device according to an exemplary embodiment.

FIG. 14 is a perspective view of a wearable device according to an exemplary embodiment. FIG. 15 is a block diagram showing elements installed in the main body of a wearable device according to an exemplary embodiment.

As shown in FIGS. 14 and 15, the biological substance estimation apparatus according to various exemplary embodiments may be implemented with a smart band-type wearable device. However, since this is merely an example for convenience of description, the exemplary embodiments should not be construed as limited only to the smart band-type wearable device.

Referring to FIGS. 14 and 15, a wearable device 1400 may include a main body 1410 and a strap composed of strap members 1413 and 1414.

The strap may be made to be flexible and may be bent in a form that surrounds a user's wrist or bent in a form with a separation from the user's wrist. In this case, a battery for supplying power to the wearable device may be disposed in the main body 1410 or the strap member 1414.

In addition, a spectrometer 1510 configured to emit light to the user's skin with light and disperse the light scattered or reflected and returned from the skin to measure a spectrum and a processor 1520 configured to estimate a biological substance in the user using the spectrum measured by the spectrometer 1510 may be disposed in the main body 1410 of the wearable device 1400.

The spectrometer 1510 may drive a light source under the control of the processor 1520 to emit light to the skin around the user's wrist and may detect the light returned from the user's skin. The light emitted from the light source reaches biological tissue via the user's skin. The light that has reached the biological tissue reacts with the biological tissue and returns. The spectrometer 1510 acquires the returned light as a spectrum and delivers the spectrum to the processor 1520. Here, the light emitted from the light source may have wavelengths in an NIR band or an MIR band.

In addition, the spectrometer 1510 may include a linear variable filter (LVF). The linear variable filter may have a spectral characteristic in which the filter linearly changes over the entire length. Accordingly, the linear variable filter may disperse incident light by wavelength. The linear variable filter has a compact size but an excellent spectral capability.

The processor 1520 may create a control signal according to a request to estimate a biological substance in a user, for example, blood sugar, and may control the spectrometer 1510.

In addition, when the spectrometer 1510 acquires the user's skin spectrum, the processor 1520 may receive data on the skin spectrum of the user from the spectrometer 1510 and may estimate the biological substance in the user using the received skin spectrum data. For example, a unit spectrum for blood sugar acquired using a serum solution or reference information needed to estimate the blood sugar, such as a reference blood sugar value, a prediction model, etc. may be stored in advance in a storage module (e.g., a memory) installed in the wearable device 1400. The processor 1520 may estimate the blood sugar of the user by utilizing the reference information.

In addition, the processor 1520 may generate various kinds of healthcare information, such as a warning, an alarm, and a change in health state, on the basis of information regarding the estimated biological substance.

The wearable device 1400 may further include a manipulation unit (e.g., button) 1412 and a display unit (e.g., display) 1411 installed in the main body 1410.

The manipulation unit 1412 may receive a control command of a user and deliver the control command to the processor 1520 and may include a power button for entering a command to power the wearable device 1400 on/off.

Under the control of the processor 1520, the display unit 1411 may display blood substance information or additional information such as a warning or an alarm and may provide the information to the user.

In addition, the main body 1410 may include a communication interface 1530 that enables the wearable device 1400 to communicate with external devices such as a mobile terminal of the user or a unit spectrum measurement apparatus.

Under the control of the processor 1520, the communication interface 1530 may transmit necessary information to the mobile terminal of the user that may have a higher computing performance power than the wearable device 1400. In addition, the communication interface 1530 may be connected with a unit spectrum acquisition apparatus to receive a unit spectrum needed to estimate the biological substance and store the received unit spectrum in a storage device. Here, the unit spectrum may be acquired using a biological-tissue simulation solution such as a glucose serum solution.

While not restricted thereto, an exemplary embodiment can be embodied as computer-readable code on a computer-readable recording medium. The computer-readable recording medium includes any data storage device that can store data that can be thereafter read by a computer system.

Examples of the computer-readable recording medium include a read-only memory (ROM), a random-access memory (RAM), a CD-ROM, a magnetic tape, a floppy disk, an optical data storage device, and also a carrier wave (such as data transmission through the Internet). The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a biological substance, the apparatus comprising:
   a spectrometer configured to emit a light to a skin of a user, detect the light returned from the skin, and measure a skin spectrum of the user from the detected light; and
   a processor configured to:
      acquire a unit spectrum by subtracting a pure spectrum from a bio substance spectrum, wherein the pure spectrum is measured from a biological tissue simulation solution including a scatterer that stimulates a light scattering phenomenon without the biological substance, and the bio substance spectrum is measured from the biological tissue simulation solution to which the biological substance is added; and
      estimate the biological substance in the user based on the measured skin spectrum and the unit spectrum.

2. The apparatus of claim 1, wherein the spectrometer measures the skin spectrum based on at least one of infrared spectroscopy and Raman spectroscopy.

3. The apparatus of claim 1, wherein the biological tissue simulation solution further comprises at least one of gelatin, silica, intralipid, and a serum solution.

4. The apparatus of claim 1, wherein the processor comprises:
   a prediction model creator configured to collect a background spectrum of the user as learning data and create a prediction model of the biological substance using the collected learning data; and
   a substance estimator configured to estimate the biological substance using the prediction model.

5. The apparatus of claim 4, wherein the substance estimator is further configured to estimate the biological substance based on a reference value of the biological substance, the unit spectrum, and an output result of the prediction model.

6. The apparatus of claim 4, wherein the spectrometer measures the background spectrum from the user's skin in a fasting state in a preset calibration cycle or upon receiving a request from the user.

7. The apparatus of claim 1, wherein the biological substance comprises at least one of a blood substance and a skin substance,
   the blood substance comprises at least one of blood sugar, cholesterol, neutral fat, proteins, and uric acid,
   the skin substance comprises at least one of body fat and proteins, and
   the proteins comprise at least one of collagen, keratin, and elastin.

8. The apparatus of claim 1, further comprising an output unit configured to output a result of estimating the biological substance.

9. The apparatus of claim 1, further comprising a main body comprising the spectrometer and the processor,
   wherein the main body is wearable by the user.

10. The apparatus of claim 9, wherein the main body further comprises a display configured to display a result of estimating the biological substance to the user.

11. The apparatus of claim 9, wherein the main body further comprises a communication interface configured to connect the apparatus to an external device via wired or wireless communication and receive the unit spectrum from the external device.

* * * * *